US006399750B1

(12) United States Patent
Johansson

(10) Patent No.: US 6,399,750 B1
(45) Date of Patent: *Jun. 4, 2002

(54) IGG SEPARATION MEDIUM

(75) Inventor: Ingemar Johansson, Uppsala (SE)

(73) Assignee: Pharmacia Biotech AB, Uppsala (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/896,507

(22) Filed: Jun. 9, 1997

Related U.S. Application Data

(63) Continuation of application No. PCT/SE96/01430, filed on Nov. 6, 1996.

(30) Foreign Application Priority Data

Nov. 7, 1995 (SE) ............................................. 9503925

(51) Int. Cl.$^7$ ........................... A23J 1/00; C07K 16/00; G01N 33/543
(52) U.S. Cl. ..................... 530/413; 530/412; 530/387.1; 530/389.1; 530/391.1; 530/812; 530/813; 530/814; 530/815; 530/816; 530/817; 530/402; 436/518; 436/528; 436/529; 436/530; 436/531; 436/532
(58) Field of Search ................................. 530/412, 413, 530/387.1, 389.1, 391.1, 812, 813, 814, 815, 816, 817, 402; 436/518, 528, 529, 530, 531, 532

(56) References Cited

U.S. PATENT DOCUMENTS

| 4,977,247 A | 12/1990 | Fahnestock et al. | |
|---|---|---|---|
| 5,089,605 A | 2/1992 | Profy et al. | ................. 530/402 |
| 5,229,492 A | 7/1993 | Fahnestock | ................. 530/350 |
| 5,362,859 A | 11/1994 | Zale | ........................... 530/314 |

FOREIGN PATENT DOCUMENTS

| EP | 0284368 | 9/1988 |
|---|---|---|
| EP | 0383620 | 2/1990 |
| EP | 0444514 | 9/1991 |
| WO | 9209633 | 6/1992 |

OTHER PUBLICATIONS

He et al, Science, vol. 251(5000), pp. 1479–81 (1991). (Only the abstract is enclosed).*
Eur. J. Biochem, vol. 186, 1989, Charlotta Ljungquist et al, "Thiol–directed immobilizatin of recombinant IgG–biding receptors", p. 557 –p. 561.

* cited by examiner

*Primary Examiner*—Padmashri Ponnaluri
(74) *Attorney, Agent, or Firm*—Gilberto M. Villacorta; Corinne M. Pouliquen; Katten Muchin Zavis Rosenman

(57) ABSTRACT

A separation medium having a base matrix and matrix-bound groups which exhibit recombinant Protein A containing a cysteine. The groups are of formula:

—B—X—rProtein A-cys where B is a bridge which binds to the base matrix and X includes a heteroatom N or S from rProtein A-cys. In a preferred embodiment X is a thioether sulphur and/or a secondary amine (—NH—). An alternative embodiment features a variant of Protein A in which the C-terminal residue is cysteine.

17 Claims, No Drawings

IGG SEPARATION MEDIUM

REFERENCE TO RELATED APPLICATION

This Application is a continuation of International Application No. PCT/SE96/01430, whose international filing date is Nov. 6, 1996, which in turn claims the benefit of Swedish Patent Application No. SE9503925-1, filed Nov. 7, 1995, the disclosures of which Applications are incorporated by reference herein. The benefit of the filing and priority dates of the International and Swedish Applications is respectfully requested.

1. FIELD OF THE INVENTION

The present invention relates generally to methods of preparing and using a separation medium for purifying IgG. In particular, the present invention relates to the preparation and use of Protein A and variants of Protein A, including recombinantly produced variants, to purify IgG by coupling the Protein A or variant thereof to a base matrix with a bridging group.

2. BACKGROUND OF THE INVENTION

Adsorbents which exhibit IgG-binding proteins have been used to capture IgG in aqueous media for more than twenty years. Initially, native Protein A (GB 1,441,979 (Sjöqvist)) was used. Later recombinantly produced forms of Protein A and were developed (WO 8400773 to Lofdahl, et al.; EP 262,192 to Guss, et al.; and U.S. Pat. No. 5,082,773 to Fahnestock).

Protein A has a broad IgG-specificity with respect to animal species, but the specificity may vary with respect to subclasses (for instance, human IgG3 will not bind to Protein A). Protein G binds to all IgG subclasses of a majority of important mammalian species. The advantage of Protein A compared to Protein G is that the binding of IgG is weaker, and consequently milder conditions can be used to release IgG from Protein A. This is of importance for the purification of individual monoclonal antibodies.

Recombinant techniques enable simple mapping of IgG-binding proteins with regard to the functionality of different domains. In the case of Protein A, it was found that the native form contained five consecutively ordered IgG-binding C domains (E, D, A, B and C), followed by an X-domain which did not bind IgG. The new technique facilitated the preparation of IgG-binding fragments and variants where one or more amino acids was/were replaced, added or removed. Unless otherwise indicated, reference to Protein A indicates the native form, or IgG-binding fragments and variants of Protein A that have the same IgG specificity as native Protein A. Variants of Protein A which contain cysteine were produced relatively early on, and the inserted cysteine residue was used for binding to base matrices. It was considered important not to place cysteine as a C-terminal residue. A variant having cysteine as the penultimate amino acid in the C-terminal part was bonded to activated Thiol SEPHAROSE® (Pharmacia Biotech AB, Uppsala, Sweden) via disulfide bond formation and studied as an IgG-separation medium (T. Profy (Repligen); EP 284,368 and U.S. Pat. No. 5,084,559). Similar studies were also presented in FASEB 87, Mar. 29–Apr. 2, 1987 (Poster N44, Profy, et al). The results obtained with three other variants (1, 2 and 5 domains) of Protein A with cysteine in a C-terminal linker sequence (amino acid 10 from the C-terminal) (Ljungquist, et al, Eur. J. Biochem. 186 (1989) 557–561) were later presented. These latter variants were also coupled covalently via disulfide bound formation to thiopropyl SEPHAROSE®. Immobilization to tresyl chloride or tosyl chloride activated gels was suggested as an alternative, with the intention of avoiding reductively sensitive linking groups. An equimolar relationship was found between IgG binding capacity and the number of domains for one-domain and two-domain variants. The five-domain variant never bonded more than the double molar amount of IgG. IgG-capacities comparable to those achieved earlier with soluble forms of native Protein A were obtained it was later found that in certain applications, non-cys-containing variants can give molar binding ratios which lie between two and three).

Parallel herewith, Genex (U.S. Pat. No. 4,977,247 (Fahnestock, et al) has produced a recombinant variant of rProtein G-cys in which cysteine is located at the C-terminal end of an IgG-binding domain. In preparing separation media based on this Protein G variant, the choice was to bind rprotein G-cys covalently to aminohexyl-agarose activated with the bi-functional reagent N-sulfosuccinimidyl-4-(p-maleimidophenyl) butyrate (U.S. Pat. No. 4,977 247, Claim 1 and column 18, lines 22–37). GAMMABINDG® Plus (Pharmacia Biotech AB) is a commercially available solid phase rProtein G-cys product with cysteine as the C-terminal residue. The product is synthesized by coupling the cysteinyl residue to aminohexyl agarose activated with N-sulfosuccinimidyl 4-(N-maleimidomethyl) cyklohexane-1-carboxylate.

As far as we are aware, the variant of the matrix-bound rProtein A-cys produced by Repligen has not found favor commercially. The reason may be that the coupling to the matrix is through unstable structures (—S—S—), although the reason may also be due to factors unknown to us. Whatever the reason, however, the adsorbent that totally dominates commercially makes use of native Protein A or different forms of recombinant Protein A that lack cysteine. The market for products based on Protein G has been substantially smaller, probably because Protein A has more advantageous binding properties.

3. SUMMARY OF THE INVENTION

The object of the invention can be summarized in the desire to provide adsorption media which have a) the IgG-binding specificity of Protein A; b) at least the same stability as other adsorbents based on native Protein A; c) the same or improved capacity to bind IgG. compared to earlier known variants of matrix bound rProtein A-cys (primarily calculated as the ratio mol IgG per mol cys-variant of Protein A with one, two or more IgG binding domains). For variants with two or more domains this means molar ratios ≧2. Fulfillment of these objects will enable more effective processes to be used for purifying IgG from different starting materials.

4. DESCRIPTION OF THE PREFERRED EMBODIMENTS

The main aspect of the invention is a separation medium which comprises a base matrix substituted with groups of the formula I:

—B—X—rProtein A-cys,     I where
  a. rProtein A-cys is recombinantly produced Protein A which contains cysteine in its amino acid sequence;
  b. B is a bridge which binds to the base matrix; and
  c. X contains a heteroatom N or S originating from rProtein A-cys.

The characteristic feature is that X is a thioether sulphur (—S—) and/or a secondary amine (—NH—); i.e. in one and the same separation medium X may be either or both a thioether sulphur and/or a secondary amine, with preference for greater than 50%, such as essentially 100%, of all X being thioether sulphur.

The optimal molar ratio between the total IgG binding capacity and the amount of Protein A on the matrix may vary depending on the number of IgG-binding domains that are present in the Protein A of the adsorbent. For single-domain variants the ratio is 1 and for 2-domain variants the ratio is ≈2. For three-, four- and five-domain variants the ratio is ≈2 or preferably >2. The maximum value is determined by the number of IgG-binding domains and is therefore contingent on the particular Protein A construction used.

In principle, B can be anything that has satisfactory stability under the conditions applied in the adsorption/desorption of IgG (time, temperature, pH, etc.). Examples of relevant structures in the bridge —B— are amide, ester, ether, thioether, hydrocarbon chains, azo, carbamate, etc. Hydrocarbon chains present in —B— may be straight, branched or cyclic, and normally have only saturated carbon atoms (2–10 carbon atoms, preferably 2, 3 or 4 carbon atoms to retain a pronounced hydrophilic nature). It is preferred that bridge —B— binds to the base matrix via an ether structure or an amide/ester structure. It is also preferred that B comprises a straight, branched or cyclic saturated hydrocarbon chain which may optionally compromise at one or more positions in the hydrocarbon chain an inserted oxygen or nitrogen, or at one or more positions in the hydrocarbon chain a hydrogen substituted with an amino or a hydroxy group. For stability reasons one and the same carbon atom should bind at most one oxygen or nitrogen atom. The structures that are preferred in —B— are those which occur when rProtein A-cys is coupled to the matrix via an epoxy group or epihalo; i.e. —B— includes at the end nearest X, the structure

—CH$_2$—CHOH—CH$_2$—

X becomes a secondary amine or thioether, depending on whether the ε-amino group in a lysine, an N-terminal amino group, or a thiol group in cysteine (preferably located at/or near the C-terminal end) is coupled.

The aforesaid bridge structures can be formed in accordance with current techniques, for instance by the use of bi-functional coupling reagents, such as epichlorohydrin, bisepoxide (such as 1,4-bis (2,3-epoxypropoxy) butane, N-sulfosuccinimidyl 4-(N-maleimidomethyl)-cyklohexane-1-carboxylate, etc. Relevant base matrices may be activated with such reagents, so that they will contain groups that react more or less selectively with thiol or amino groups. Preferred coupling reagents and conditions give very little coupling at primary amino groups (ε-amino in lysyl and N-amino terminal groups).

Relevant forms of rProtein A-cys have an amino acid in the native sequence replaced with cysteine. Alternatively, cysteine can be present in an amino acid sequence (linker) which has been fused to a terminal, or as an insert in the native sequence or an IgG-binding part thereof. Cysteine may also be included in a peptide linker that preferably is N-terminal or C-terminal to an IgG-binding domain. Generally speaking, a terminal cysteine is preferred to an internal cysteine. The length of the linker used is normally not critical and may vary from one to fifty amino acid residues, for instance. For all cysteine modifications it is imperative that the IgG binding ability is not lost or reduced substantially.

rProtein A-cys may also, be modified in other ways. For example, rProtein A-cys may be a fusion protein which, in addition to featuring an IgG-binding domain from Protein A, also includes one or more IgG-binding domains from Protein G or from some other IgG-binding protein (c.f. Guss, et.al, EP 262, 192). The native domains maybe permutated, occur one or more times, or some may be deleted. Native non-IgG-binding domains may be missing totally or in part.

rProtein A-cys can be prepared in accordance with current techniques (Profy T, EP 294,386; and Ljungquist, et al, Eur. J. Biochem. 186 (1989), 557–561).

The base matrix is a hydrophilic polymer which contains a plurality of amino groups and/or hydroxy groups, primarily the latter. The base matrix is normally insoluble in aqueous media. The base matrix may originate from a polysaccharide, such as dextran, cellulose, starch, agarose, pullulan, xylan, etc., which may be cross-linked and/or provided with different groups suitable for the use intended. Among synthetic polymers can be mentioned polymers of hydroxyalkyl acrylates or corresponding methacrylates, polyvinyl alcohols, polymers of vinyl hydroxyalkyl ethers, etc. To the extent that a polymer is soluble, it can be made insoluble, for instance crosslinked or adsorbed or covalently bound to a support which is insoluble in aqueous media, for instance a styrene divinyl benzene copolymer. The base matrix can also be in the form of particles that may be more or less spherical and/or porous or non-porous. One particular type of matrix is porous hydrophobic particles made of divinyl benzene-styrene copolymer or some other hydrophobic polymer/copolymer, the inner and/or outer surfaces of which have been hydrophilized and provided with OH-groups. In a preferred embodiment, the matrix is insoluble in aqueous media, porous and based on a polysaccharide.

Another main aspect of the invention involves binding (adsorbing) IgG to a separation medium. IgG is then contacted with a separation medium in accordance with the aforegoing. Adsorption normally takes place from an aqueous solution derived from serum or a cell culture capable of producing IgG. Suitable conditions lie in the range 0–35° C., pH 6–8, salt concentration 0.1–3 M (depending on the type of IgG to be bound). Before desorption of bound IgG, the separation media are normally washed, suitably with a buffer essentially with the same pH as the adsorption buffer, whereafter desorption is effected conventionally, for instance by treatment with a buffer which has a pH beneath 5. The conditions should be non-denaturing.

Binding of IgG to the separation medium has a broad field of use. It can be utilized in processes involving capture of IgG from a solution, i.e. to separate IgG dissolved in an aqueous solution from other components present therein. Binding of IgG may be a part-step in a chromatography process or in a batch-wise process. Binding of IgG may also be a part of a so-called immunoassay or an extracorporeal process for removing IgG from whole blood or plasma. The primary area of use is found in purifying IgG (including monoclonal IgG antibodies).

A very expedient embodiment of the invention is to couple rProtein A-cys by a C-terminal cysteine to a chromatographic particulate matrix containing densifying filler particles, such as ANVAL® (Anval, Torshälla, Sweden). The so obtained chromatographic support has been found very useful for chromatographic separations of IgG in stabilised fluidised beds. See our contemporary patent application SE 9503926-9 relating to "Adsorption Method and Separation Medium". With regard to chromatography on expanded/fluidized beds, reference is made to WO 9218237 (Pharmacia Biotech AB).

5. EXAMPLES AND PROCEDURES

5.1. Preparation of rProtein A-cys rProtein A-cys was prepared in accordance with the description given in EP 284,368 or by Ljungqvist, et al, Eur. J. Biochem. 186 (1989), 557–561. The sequence was the same as that disclosed in EP 284,365, with the exceptions that (1) the first 18 amino acids were deleted (signal sequence), and (2) the last 103, amino acids were replaced with a hexapeptide sequence with cysteine as C-terminal.

5.2. Coupling of a rProtein A-cys to Base Matrix 5.2.1 Activating with the aid of of 1.4 bis(2,3-epoxy propoxy) butane (BPR-butane). One litre of drained SEPHAROSE® FF (agarose in bead form cross-linked with epichlorohydrin, Pharmacia Biotech AB, Uppsala, Sweden) was washed on a filter funnel with distilled water and admixed with 55 g NaOH dissolved in 300 ml distilled water, 35° C., in a thermostat-controlled reaction vessel while stirring the system. 390 ml BPR-butane were added. The system was stirred for two hours at 35° C., followed by washing with 15 water.

5.2.2 Coupling of a rProtein A-cys. The activated gel was washed on a filter funnel with 3×1 l nitrogen-gas saturated 0.1 M Na-phosphate, 1 mM EDTA pH 8.5, and was allowed to drain. The gel was then mixed with 5.5 g rProtein A-cys dissolved in a nitrogen-gas saturated aqueous solution of 0.1 M Na-phosphate, 1 mM EDTA pH 8.5. The system was stirred at 37° C. while blowing in nitrogen gas. Sodium sulphate (370 g) was added. After stirring the system for two hours at 37° C., the gel was washed with 3 l distilled water and drawn-off by suction.

5.2.3 Deactivation. The drawn-off gel was mixed with 100 ml thioglycerol dissolved in 900 ml 0.2 M sodium bicarbonate, 0.5 M NaCl, 1 mM EDTA pH 10, while stirring the system. The system was stirred overnight at 37° C., whereafter the gel was washed on a filter funnel with 0.1 M Tris, 0.15 M NaCl, pH 8, and 0.05 M acetic acid in three cycles with 3×1 gel volume in each cycle. The gel was washed finally with water.

5.3 Determining the Total Binding Capacity of Human IgG

Instrument: FPLC with superloop (Pharmacia Biotech AB).
Column: 1 ml HR 5/5 (Pharmacia Biotech AB).
Buffer A: 10 mM sodium dihydrogenphosphate, 0.15 M sodium chloride, 10 mM EDTA, pH 7.
Buffer B: 0.5 M acetic acid (gives a pH of about 2.7).
IgG-solution: 150 mg human IgG in 10 ml buffer A (centrifuged and filtered).
Printer speed: 0.05–0.25 cm/min.

1.0 ml of drained gel was packed in the column and equilibrated with buffer A. The IgG-solution was delivered through the superloop at a flow rate of 0.15 ml/min., until the gel was saturated with respect to IgG. After washing with buffer A at the same rate of flow, bound IgG was eluted with 9 ml buffer B at a flow rate of 0.30 ml/min. The eluate with buffer B was collected and its volume determined (weighed). $A_{280}$ was determined for each sample a 1:10 dilution. The formula applied in determining the IgG binding capacity was: Eluate volume in ml×$A_{280}$ or dilute eluate×7.244=mg IgG/ml of drained gel.

5.4 Determining the Breakthrough Capacity $Q_B$ for Human IgG

Column: XK 16/20 (Pharmacia Biotech AB).
Buffer A: 20 mM Na-phosphate, pH 7.0.
Buffer B: 0.1 M glycine, pH 3.0.
IgG-solution: About 0.5 g IgG per l in Buffer A.
Flow rate: 10 ml/min. (300 cm/h).
Printer speed: 0.02 cm/ml.
Column volume: 23 ml.

Delivery of IgG solution was interrupted when $c/c_0$ measured in the eluate had reached 1% (c and $c_0$ are protein concentrations, respectively, in eluent subsequent to and prior to passage of the column). Adsorbed IgG was then eluated with buffer B and its volume determined as mg IgG per ml of drained gel.

Results and conditions for the coupling experiment that gave the highest dynamic capacity were: Na-sulphate 1.3 M; charged quantity of rProtein A-cys 7.1 mg/ml gel; coupling buffer pH 8.5; coupling temperature 37° C.; coupling time 2 hours; total capacity 52.2 mg IgG per ml gel; breakthrough capacity 31.3 mg per ml gel at $c/c_0=1\%$. Largely comparable dynamic capacities could be obtained in trials where 5–6 mg rProtein A-cys were charged for each ml gel.

5.5 Other Coupling Methods

Epoxy-coupling of rProtein A-cys-was compared with native Protein A (lacks cysteine) coupled to N-hydroxysuccinimide (NHS) and rProtein A-cys coupled to N-sulfosuccinimidyl 4-(N-maleimidomethyl) cyclohexane-1-carboxylate (Sulfo-SMCC). In coupling native Protein with NHS or epoxide, coupling is effected solely via an amino group. In the case of the reagent Sulfo-SMCC, coupling of rProtein A-cys is effected via a thiol group. In coupling rProtein A-cys with epoxy (BPR), coupling can be effected both to a thiolgroup and to an amino group, the preference being determined by pH. At comparable degrees of substitution, the total capacity increased in the order NHS, epoxy, Sulfo-SMCC. The differences are probably due to steric effects caused by amine coupling via groups that are not seated terminally. Comparison tests with rProtein G and rProtein G-cys are also reported below.

TABLE 1

Capacity of human IgG for different coupling methods applied on SEPHAROSE ® FF[1])

| | Subst deg nmol/ml gel | Tot cap mg IgG/ml | $Q_B$ gel | Mol IgG/ mol Prot A |
|---|---|---|---|---|
| 387758A[2]) NHS Prot A | 104 | 23.8 | ND[3]) | 1.5 |
| 387789[2]) SulfoSMCC, rProt A-cys | 100 | 44.7 | 32 | 2.9 |
| 441713A1[2]) Epoxy, rProt A-cys | 100 | 35.2 | ND[3]) | 2.3 |

TABLE 2

Capacity of human IgG to bind to Protein G adsorbents

| | Subst deg nmol/ml gel | Tot cap mg IgG/ml | Mol IgG/ mol Prot A |
|---|---|---|---|
| 35169[2]) GAMMABINDG ®[1,4]) Type 2 CNBr, SEPHAROSE ® 4B[1]) | 145 | 23.3 | 1.03 |

TABLE 2-continued

Capacity of human IgG to bind to Protein G adsorbents

|  | Subst deg nmol/ml gel | Tot cap mg IgG/ml | Mol IgG/ mol Prot A |
|---|---|---|---|
| 35170[2]) GAMMABINDG ®[1,4)] Type 3 SulfoSMCC, SEPHAROSE ® CL6B[1)] | 220 | 41.5 | 1.2 |
| 35174[2)] GAMMABINDG ®[1,4)] Type 2 NHS, SEPHAROSE ® 6FF[1)] | 204 | 26 | 0.8 |

[1)]Pharmacia Biotech AB,
[2)]Internal journal number,
[3)]Not specified,
[4)]GAMMABINDG ® Type 2 is Protein G and GAMMABINDG ® Type 3 is Protein G with cysteine as C-terminal. Both variants have two IgG-binding domains.

The results show that a very good total binding capacity and break-through capacity were achieved, and that the binding capacity in mol IgG per mol rProtein A-cys was far above that earlier achieved for cys-containing IgG-binding proteins.

5.6 The Breakthrough Capacity for Human IgG Comparison Studies for Different Protein A Adsorbents 5.6.1 Methodology: Protein A matrices (rProtein A SEPHAROSE® Fast Flow (this invention, immobilization via epoxy); Protein A SEPHAROSE® 4 Fast Flow (immobilization via CNBr, Pharmacia Biotech AB); PROSEP A® (Bioprocessing Ltd., UK) and Protein A Hyper D® (BioSepra S.A., France) were packed in XK 16/20 columns to a bed height of 10 cm. The gels were equilibrated in 20 mM phosphate buffer, pH 7.4. A sample consisting of human polyclonal IgG (1 mg/ml) in the same buffer was delivered to respective gels in the linear flow 190 cm/h. Sample delivery was interrupted when the concentration of IgG in the eluate had reached 10% of the initial IgG concentration of the sample solution. Non-bound IgG was washed out and the bound IgG eluated with 0.1 M citrate, pH 3. The breakthrough capacity $Q_B$ was calculated as the amount of IgG that had bound per ml of gel when the IgG concentration in the eluate was 5% of the initial IgG concentration in the sample.

The concentration of Protein A in the eluated IgG fraction was determined with ELISA. The amount of Protein A in the IgG fraction is given as ng protein A/mg IgG.

5.6.2 Results

| Protein A matrix | $Q_B$ (mg/ml) | Protein A in IgG-fraction (ng/mg) |
|---|---|---|
| rProtein A-cys SEPHAROSE ® FF | 40 | 11 |
| Protein A SEPHAROSE ® 4 FF | 23 | 8 |
| PROSEP A ® | 24 | 266 |
| Protein A Hyper D ® | 27 | Not analyzed. |

These values show that the invention enables the construction of Protein A adsorbents whose breakthrough capacities are higher than other commercially available matrices. Compared to the same matrices, the stability with regard to the release of Protein A is roughly the same or better.

What is claimed is:

1. A separation medium comprising:

a base matrix; and matrix-bound groups having the formula:

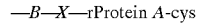

—B—X—rProtein A-cys where

B is a bridge which binds to the base matrix and to X,

X is selected from the group consisting of secondary amine (—NH—) and thioether sulphur (—S—), and rProtein A-cys comprises a recombinant Protein A having a cysteine in its amino acid sequence.

2. The separation medium of claim 1, where greater than 50 percent of the matrix bound groups have X equal to thioether sulpher (—S—).

3. The separation medium of claim 2, where an ether structure binds the base matrix to the bridge, and where the bridge is a straight, branched, or cyclic saturated hydrocarbon chain.

4. The separation medium of claim 1, where the bridge comprises the structure —$CH_2$—CHOH—$CH_2$—.

5. The separation medium according to claim 2, where the cysteine is located in a terminal peptide linker of the rProtein A-cys.

6. The separation medium according to claim 2, where the cysteine is located in a C-terminal peptide linker of the rProtein A-cys.

7. The separation medium according to claim 2, where the cysteine is the C-terminal amino acid residue in the rProtein A-cys.

8. The separation medium according to claim 2, where the base matrix comprises a polyhydroxy polymer.

9. The separation medium according to claim 8, where the polyhydroxy polymer comprises an insoluble polysaccharide.

10. The separation medium according to claim 8, where the polyhydroxy polymer is selected from the group consisting of dextran, cellulose, starch, agarose, pullulan, xylan, hydroxyalkyl acrylate polymers, hydroxyalkyl methacrylate polymers, polyvinyl alcohol polymers, and vinyl hydroxyalkyl ether polymers.

11. The separation medium according to claim 1, where the bridge comprises structures selected from the group consisting of amide, ester, ether, thioether, hydrocarbon chains, azo, and carbamate.

12. The separation medium according to claim 1, where the base matrix is insoluble in aqueous media.

13. The separation medium according to claim 1, where the base matrix comprises particles.

14. The separation medium according to claim 13, where the particles comprise densifying filler particles.

15. The separation medium according to claim 1, where the rProtein A-cys comprises at least two IgG binding domains.

16. The separation medium of claim 3, wherein the bridge comprises structures selected from the group consisting of amide, ester, ether, thioether, hydrocarbon chains, azo, and carbamate.

17. The separation medium of claim 1, wherein the rProtein A-cys comprises a hexapeptide sequence with cysteine as the C-terminal amino acid residue.

* * * * *